United States Patent
Duan et al.

(10) Patent No.: US 11,421,083 B2
(45) Date of Patent: Aug. 23, 2022

(54) PETX POLYMER, PREPARATION METHOD AND THREE-DIMENSIONAL THORN-LIKE SENSOR INTERFACE

(71) Applicant: TIANJIN UNIVERSITY, Tianjin (CN)

(72) Inventors: Xuexin Duan, Tianjin (CN); Wenwei Pan, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 17/595,272

(22) PCT Filed: May 14, 2020

(86) PCT No.: PCT/CN2020/090348
§ 371 (c)(1),
(2) Date: Nov. 12, 2021

(87) PCT Pub. No.: WO2020/238643
PCT Pub. Date: Dec. 3, 2020

(65) Prior Publication Data
US 2022/0213275 A1 Jul. 7, 2022

(30) Foreign Application Priority Data
May 31, 2019 (CN) .......................... 201910472850.4

(51) Int. Cl.
*C08G 81/00* (2006.01)
*G01N 33/48* (2006.01)
(Continued)

(52) U.S. Cl.
CPC ..... *C08G 81/028* (2013.01); *G01N 33/54373* (2013.01)

(58) Field of Classification Search
CPC .......................... C08G 81/028; G01N 33/54373
(Continued)

(56) References Cited

U.S. PATENT DOCUMENTS

| 2005/0164895 A1 | 7/2005 | Spencer et al. |
| 2006/0094673 A1 | 5/2006 | Chu |

FOREIGN PATENT DOCUMENTS

| CN | 1345301 A | 4/2002 |
| CN | 1646912 A | 7/2005 |

(Continued)

OTHER PUBLICATIONS

Chao Deng et al. ["A biodegradable triblock copolymer poly(ethylene glycol)-b-poly(L-Lysine):Synthesis, self-assembly, and RGD peptide modification," Polymer, vol. 48, No. 5, Nov. 28, 2006, pp. 139-149] (Year: 2006).*

(Continued)

*Primary Examiner* — Kelechi C Egwim
(74) *Attorney, Agent, or Firm* — John A. Miller; Shumaker, Loop & Kendrick, LLP

(57) ABSTRACT

A PETx polymer including a main backbone which is a first poly-L-lysine, and a side chain which is sequentially connected with a first polyethylene glycol and a second poly-L-lysine, where the second poly-L-lysine is saturately connected with a second polyethylene glycol and a third polyethylene glycol with no remaining amino groups, and the third polyethylene glycol is connected with a functional group at its end, where the first poly-L-lysine and the second poly-L-lysine have the same or different chain lengths, and the first polyethylene glycol, the second polyethylene glycol and the third polyethylene glycol have the same or different chain lengths. Preferably, the PETx polymer is PLL-g-{PEGk-PLL-g-[(PEGj-biological recognition group)y %(PEGi)1-y %]}x %, where i, j, k, m, and n are all integers greater than or equal to 1, j is not equal to i, and x and y are all greater than 0 and less than 100.

9 Claims, 10 Drawing Sheets

(51) Int. Cl.
*C08G 81/02* (2006.01)
*G01N 33/543* (2006.01)

(58) Field of Classification Search
USPC .......................................................... 525/54
See application file for complete search history.

(56) References Cited

FOREIGN PATENT DOCUMENTS

| | | |
|---|---|---|
| CN | 108957010 A | 12/2018 |
| CN | 110183672 A | 8/2019 |
| EP | 3329945 A1 | 6/2018 |
| WO | 2004038040 A2 | 5/2004 |
| WO | 2004038040 A3 | 1/2005 |
| WO | 2018234564 A1 | 12/2018 |

OTHER PUBLICATIONS

Xiufang Wen et al. ["Specific antibody immobilization with biotin-poly(L-lysine)-g-poly(ethylene glycol) and protein A on microfluidic chips," Journal of Immunological Methods, vol. 350, No. 1-2, Aug. 6, 2009, pp. 97-105] (Year: 2009).*

Chao Deng et al. "A biodegradable triblock copolymer poly(ethylene glycol)-b-poly(L-Lysine):Synthesis, self-assembly, and RGD peptide modification," Polymer, Nov. 28, 2006, pp. 139-149, vol. 48, No. 5.

Xiufang Wen et al. "Specific antibody immobilization with biotin-poly(L-lysine)-g-poly(ethylene glycol) and protein A on microfluidic chips,", Journal of Immunological Methods, Aug. 6, 2009, pp. 97-105, vol. 350, No. 1-2.

* cited by examiner

PETX POLYMER, PREPARATION METHOD AND THREE-DIMENSIONAL THORN-LIKE SENSOR INTERFACE

CROSS-REFERENCE TO RELATED APPLICATIONS

This application is a National Stage application of International Application No. PCT/CN2020/090348 filed on May 14, 2020, which claims priority to Chinese Application No. 201910472850.4 filed May 31, 2019.

BACKGROUND

Field

The invention relates to a PETx polymer, a preparation method and a three-dimensional thorn-like sensor interface based on the PETx polymer.

Discussion of the Related Art

For surface-based biosensors, surface activation methods are often used to make the surface of a sensor have specific functions (for example, anti-nonspecific adsorption function and specific biological recognition function). There are mainly two kinds of such surface activation according to the connection method between the sensor surface and the functionalized material: covalent connection method and non-covalent connection method.

Covalent attachment methods have many disadvantages, including: 1) covalent attachment (such as amino coupling) may interfere with a protein's structure and affect its binding behavior; 2) it is difficult to control direction and surface density of a protein; 3) the hydrolysis of the silane bond will destroy the long-term stability of the functional group; and 4) the covalent bond is irreversible and the sensor can only be used once.

For various surface-based biosensors, most of the sensing surfaces are composed of Au and metal oxides such as $Si/SiO_2$, which carry slight negative charges (under physiological pH). Poly-L-lysine (PLL) is a polypeptide with very clear toxicological significance. It has a high cationic nature at physiological pH, so it is often used as a polymer backbone for synthesis of polyelectrolytes. This kind of polyelectrolyte with PLL as the backbone is positively charged due to the amino groups on the PLL, which can be modified to the negatively charged sensor surfaces by means of electrostatic action, so that the surface of the sensor has a specific function.

Biotin-Streptavidin-System (BAS) is a new type of biological reaction amplification system developed at the end of the 1970s, which can be combined with various markers that have been successfully studied. Therefore, in the field of biosensing, biotin is often used as a functional group for specific adsorption of streptavidin (SAv).

PLL-g-PEG-Biotin is an invented functionalized material. Its structure diagram is shown in FIG. 1, which is a brush-like polymer. The polymer uses PLL as the backbone, and the main body of the side chain is PEG (polyethylene glycol), and biotin is used as a functional group, more precisely, a biological recognition group at the end of the side chain. It is positively charged at physiological pH, which can be modified to the surface of the sensor through electrostatic interaction. The formed sensor interface is also called a two-dimensional sensor interface (2D interface) because the functional groups are on the same plane. The modified sensor surface has the functions of anti-nonspecific adsorption and specific recognition and adsorption of streptavidin (SAv). In addition, by adjusting the pH, the PLL-g-PEG-Biotin can fall off from the surface of the sensor, thereby realizing the regeneration of the sensor.

One part of the amino groups on the PLL backbone is used to be grafted onto the side chain, and the other part is used to generate positive charges. Therefore, in order to ensure that the polyelectrolyte can carry enough positive charges for electrostatic modification, the side chain has a grafting ratio which is controlled below 40%, which limits the number of biological recognition groups i.e. biotin and side chain PEG per unit area, so that the specific biological recognition and anti-nonspecific adsorption capabilities of the biosensor surface are limited, thereby limiting the sensing effect of the biosensor.

SUMMARY

The present invention aims to break the limitations of the traditional 2D interface and develop a new type of polyelectrolyte material, which can form a three-dimensional functional interface (3D interface) on the surface of the sensor, while realizing the number of biological recognition groups and polyethylene glycol per unit area greatly increase.

The technical solution of the present invention is realized as follows:

As one aspect of the present invention, a PETx polymer is provided, which has a main backbone that is first poly-L-lysine, and a side chain which is sequentially connected with first polyethylene glycol and second poly-L-lysine, the second poly-L-lysine is saturately connected with second polyethylene glycol and third polyethylene glycol without remaining amino groups, and the third polyethylene glycol is connected with a functional group at its end, wherein the first poly-L-lysine and the second poly-L-lysine have same or different chain lengths, the first polyethylene glycol, the second polyethylene glycol and the third polyethylene glycol have same or different chain lengths; preferably, the PETx polymer is PLL-g-$\{PEG_k$-PLL-g-$[(PEG_j$-functional group$)_{y\ \%}(PEG_i)_{1-y\ \%}]\}_{x\ \%}$, where i, j, k are all integers greater than or equal to 1, j is not equal to i, and x and y are all in the range greater than 0 and less than 100.

The PETx polymer described herein in the present invention refers to a new type of polymer used in polyelectrolyte thin films.

Preferably, the PETx polymer is PLL-g-{PEGk-PLL-g-[(PEGj-biological recognition group)y %(PEGi)1-y %]}x %.

Preferably, the functional group is a biological recognition group (or called a biological detection group); the biological recognition group is selected from a group consisting of biotin, Ni-NTA ($Ni^{2+}$ chelated nitrilotriacetic acid) or single-stranded DNA, which is used to achieve specific biological detection functions.

As an embodiment of the present invention, the biological recognition group is biotin.

In this technical solution, the chain lengths of PLL and PEG can be arbitrary.

As an embodiment of the present invention, the grafting ratio on the first poly-L-lysine does not exceed 40%.

As an embodiment of the present invention, the molecular weight of the first poly-L-lysine is 15-30 kDa; the molecular weight of the second poly-L-lysine is 3 kDa. The molecular weights of the first poly-L-lysine and the second poly-L-lysine may have other choices depending on the taken chain length.

As an embodiment of the present invention, the PETx polymer has a following general formula:

4) grafting the polymer 4 to the main backbone poly-L-lysine with a grafting ratio not exceeding 40% to obtain polymer 5 (PETx, i.e. PLL-g-{PEG$_k$-PLL-g-[(PEG$_j$-functional group)$_{y\%}$(PEG$_i$)$_{1-y\%}$]}$_{x\%}$) (reaction 4),

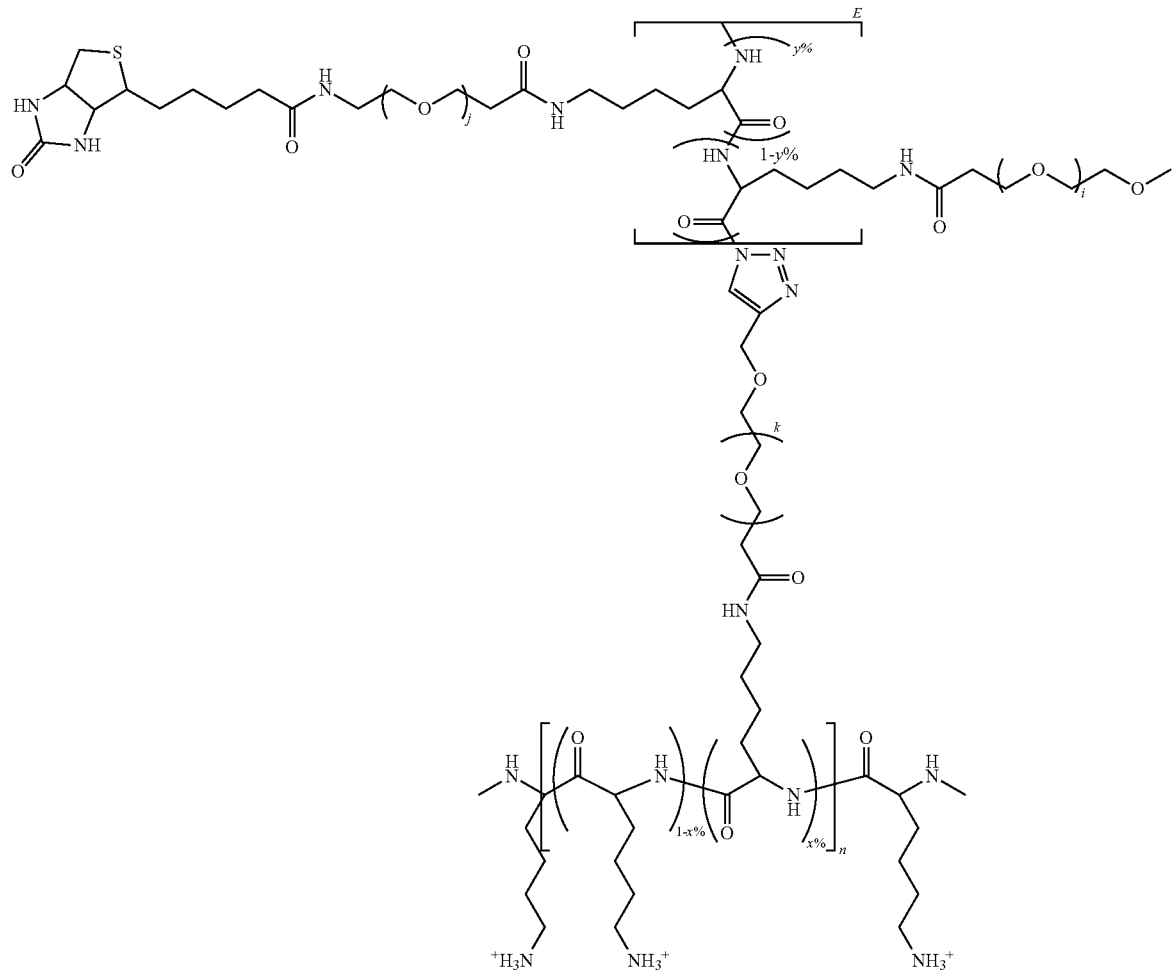

where i, j, k, m, and n are all integers greater than or equal to 1, and x and y are both in the range greater than 0 and less than 100.

As another aspect of the present invention, a preparation method of PETx polymer is provided, including the following steps:

1) by using reaction between amino groups and active ester, grafting active ester-polyethylene glycol-functional group (NHS-PEG-functional group) onto polymer 1 (N$_3$-PLL or alkynyl-PLL) to obtain polymer 2 (N$_3$-PLL-g-(PEG$_j$-functional group)$_{y\%}$ or alkynyl-PLL-g-(PEG$_j$-functional group)$_{y\%}$) (reaction 1);

2) adding excessive active ester-polyethylene glycol-methyl (NHS-PEG-methyl) to the reaction to obtain polymer 3 (N$_3$-PLL-g-[(PEG$_j$-functional group)$_{y\%}$(PEG$_i$)$_{1-y\%}$] or alkynyl-PLL-g-[(PEG$_j$-functional group)$_{y\%}$(PEG$_i$)$_{1-y\%}$]) (reaction 2);

3) by using click reaction between azide groups and alkynyl groups, grafting the polyethylene glycol-active ester (PEG-NHS) to the end of the poly-L-lysine in the polymer 3 to obtain polymer 4 (NHS-PEG$_k$-PLL-g-[(PEG$_j$-functional group)$_{y\%}$(PEG$_i$)$_{1-y\%}$]) (reaction 3);

N$_3$-PLL+NHS-PEG$_j$-biotin→N$_3$-PLL-g-(PEG$_j$-functional group)$_{y\%}$ or alkynyl-PLL+NHS-PEG$_j$-functional group→alkynyl-PLL-g-(PEG$_j$-functional group)$_{y\%}$ (1)

N$_3$-PLL-g-(PEG$_j$-functional group)$_{y\%}$+NHS-PEG$_i$-methyl→N$_3$-PLL-g-[(PEG$_j$-functional group)$_{y\%}$(PEG$_i$)$_{1-y\%}$]

or alkynyl-PLL-g-(PEG$_j$-functional group)$_{y\%}$+NHS-PEG$_i$-methyl→alkynyl-PLL-g-[(PEG$_j$-functional group)$_{y\%}$(PEG$_i$)$_{1-y\%}$] (2)

N$_3$-PLL-g-[(PEG$_j$-functional group)$_{y\%}$(PEG$_i$)$_{1-y\%}$]+NHS-PEG$_k$-alkynyl→NHS-PEG$_k$-PLL-g-[(PEG$_j$-functional group)$_{y\%}$(PEG$_i$)$_{1-y\%}$]

or alkynyl-PLL-g-[(PEG$_j$-functional group)$_y$ $_\%$ (PEG$_i$)$_{1-y}$ $_\%$]+NHS-PEG$_k$-N$_3$→NHS-PEG$_k$-PLL-g-[(PEG$_j$-functional group)$_y$ $_\%$(PEG$_i$)$_{1-y}$ $_\%$] (3)

PLL+NHS-PEG$_k$-PLL-g-[(PEG$_j$-functional group)$_y$ $_\%$(PEG$_i$)$_{1-y}$ $_\%$]→PLL-g-{PEG$_k$-PLL-g-[(PEG$_j$-functional group)$_y$ $_\%$(PEG$_i$)$_{1-y}$ $_\%$]}$_x$ $_\%$ (4)

where i, j, k, m, and n are all integers greater than or equal to 1, and x and y are both in the range greater than 0 and less than 100.

Preferably, in the preparation method of PETx polymer, the functional group is a biological recognition group, the biological recognition group is selected from a group consisting of biotin, Ni-NTA (Ni$^{2+}$ chelated nitrilotriacetic acid) or single-stranded DNA. More preferably, the biological recognition group is biotin.

Preferably, in the preparation method of the PETx polymer, the click reaction in step 3) employs a click reaction between poly-L-lysine-azide and alkynyl-polyethylene glycol-active ester to introduce the active ester or a click reaction between poly-L-lysine-alkynyl and azide-polyethylene glycol-active ester to introduce the active ester.

As one embodiment of the present invention, the preparation method of the PETx polymer includes the following steps:

1) by using reaction between amino groups on polymer 1 (N$_3$-PLL) and active ester, grafting active ester-polyethylene glycol-biotin (NHS-PEG-biotin) onto polymer 1 to obtain polymer 2 (reaction 1);

2) adding excessive active ester-polyethylene glycol-methyl (NHS-PEG-methyl) to the reaction to obtain polymer 3 to ensure that there are no remaining amino groups on the poly-L-lysine (reaction 2);

3) by using click reaction between azide groups and alkynyl groups, grafting the polyethylene glycol-active ester (PEG-NHS) to the end of the poly-L-lysine in the polymer 3 to obtain polymer 4 (reaction 3);

4) grafting the polymer 4 to the main backbone poly-L-lysine with a grafting ratio not exceeding 40% to obtain polymer 5 (PETx, i.e. PLL-g-{PEG$_k$-PLL-g-[(PEG$_j$-biotin)$_y$ $_\%$(PEG$_i$)$_{1-y}$ $_\%$]}$_x$ $_\%$) (reaction 4),

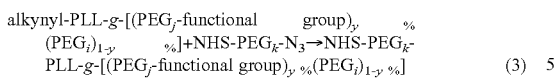
(1)

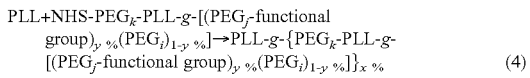
(2)

N$_3$—PLL—g—[PEG$_j$—biotin)$_{y\%}$(PEG$_i$)$_{1-y\%}$] +

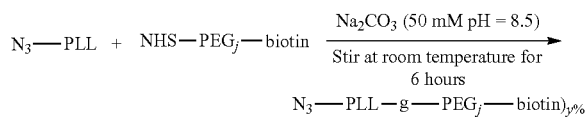
(3)

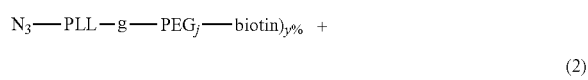

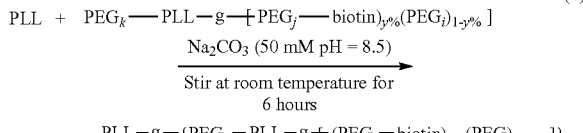
(4)

PLL—g—{PEG$_k$—PLL—g—[(PEG$_j$—biotin)$_{y\%}$(PEG$_i$)$_{1-y\%}$]}$_{x\%}$

As another aspect of the present invention, a three-dimensional thorn-like sensor interface is provided, wherein the sensor interface comprises a negatively charged sensor surface and the PETx polymer, the PETx polymer is modified to the sensor surface by means of electrostatic action, thereby forming a three-dimensional thorn-like sensing interface.

As an embodiment of the present invention, the sensor surface is an optical fiber sensor surface, a silica sensor surface, a metal sensor surface, or a metal oxide sensor surface.

As one more aspect of the present invention, use of the PETx polymer or the three-dimensional thorn-like sensor interface in biological detection and anti-nonspecific adsorption is provided.

DETAILED DESCRIPTION OF THE EMBODIMENTS

The following describes clearly and completely the technology in the embodiments of the present invention with reference to the accompanying drawings in the embodiments of the present invention. Obviously, the described embodiments are only a part of the embodiments of the present invention, but not all the embodiments. Based on the embodiments of the present invention, all other embodiments obtained by a person skilled in the art fall within the protection scope of the present invention.

The term "nonspecific adsorption" refers to a phenomenon that some biological molecules such as proteins are adsorbed to the surface of a material due to the effect of static electricity, etc., which cause interference to the experimental analysis.

The term "specific adsorption" refers to a phenomenon that a specific protein (or other biological molecule) is adsorbed to a specific active site.

The term "polyethylene glycol (PEG)" has good hydrophilicity and biocompatibility, and is widely used to resist nonspecific adsorption of proteins.

The term "click chemistry" is a concept of chemical synthesis proposed by the American chemist Karl Barry Sharpless in 2001, wherein a 1,3-dipolar cycloaddition reaction between an azide and an alkyne to give 1,2,3-triazole is the most representative. The reaction has mild conditions and provides high yield. In recent years, the applications of this reaction have gradually increased in the immobilization of proteins, especially antibodies. In one embodiment of the present invention, the click reaction between PLL-$N_3$ and alkynyl-PEG-NHS is used to introduce NHS. It should be noted that it is equally feasible to introduce NHS via the click reaction between PLL-alkynyl and $N_3$-PEG-NHS.

The following embodiments take biotin as a functional group as an example. However, the present invention is not limited to this. The functional group may also include other groups for achieving specific biological detection functions, such as Ni-NTA ($Ni^{2+}$ chelated nitrilotriacetic acid) or single-stranded DNA.

Example 1

Figure 1:
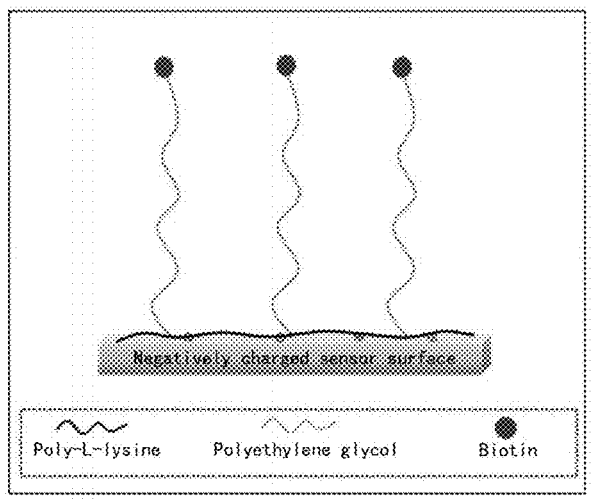
FIG. 1 is a schematic diagram of the structure of the functional material PLL-g-PEG-Biotin that has been invented in the prior art.
Figure 2:
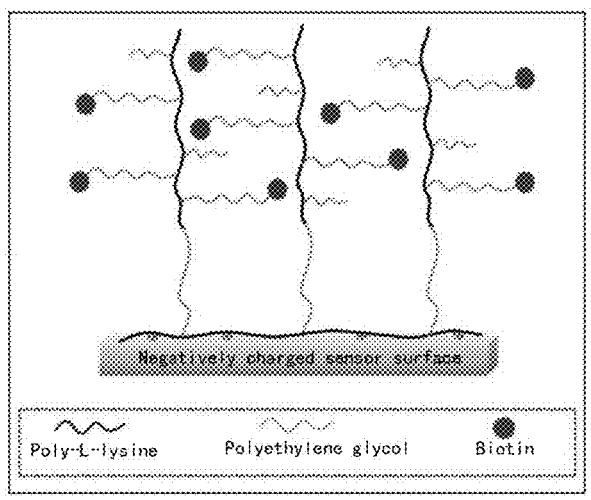
FIG. 2 is a schematic diagram of the structure of a 3D sensing interface formed by PETx whose biological recognition group is exemplified by biotin.
Figure 3:
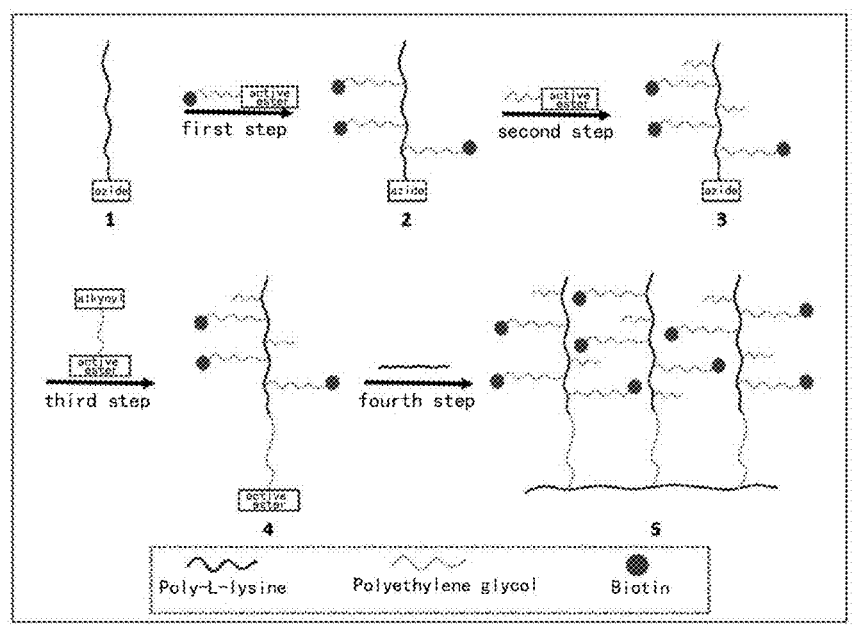
FIG. 3 is the general formula of chemical structure of PETx whose biological recognition group is exemplified by biotin.
Figure 4:
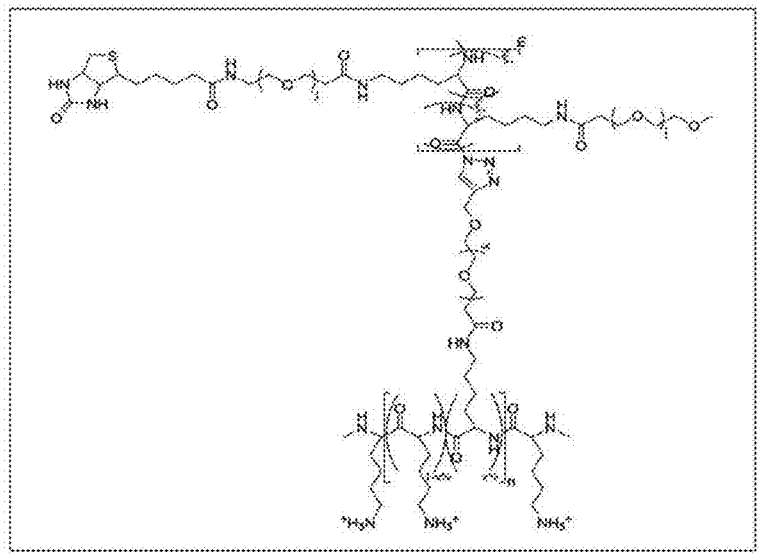
FIG. 4 is a synthesis scheme of PETx whose biological recognition group is exemplified by biotin.

FIG. 2 is a schematic diagram of a 3D sensing interface formed by PETx. PETx is composed of three parts: poly-L-lysine, polyethylene glycol and biotin. Its chemical structure is shown in FIG. 3, where i, j, k, m and n are all integers greater than or equal to 1, and x and y are all in the range greater than 0 and less than 100.

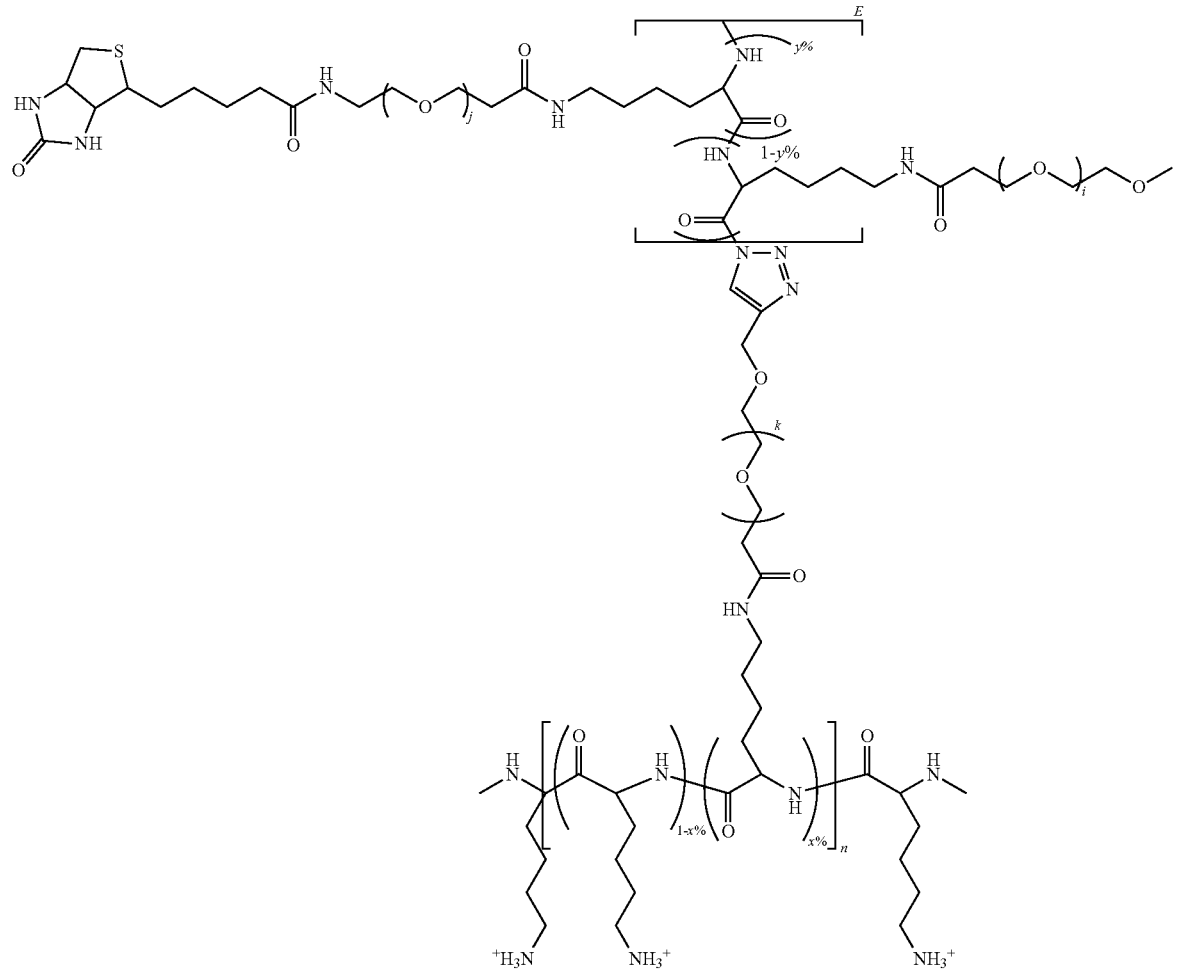

Next, the synthesis scheme of PETx is introduced by taking m=10, n=75, j=12, i=4, k=4, x=40, y=50 as an example.

Synthesis of PETx: The synthesis scheme of PETx is shown in FIG. 3. The idea of this scheme is to take the traditional 2D polyelectrolyte as a whole as a side chain and graft it onto the backbone of poly-L-lysine to form a 3D polyelectrolyte PETx. In order to facilitate the introduction of active ester (NHS) groups that can react with amino groups, we chose poly-L-lysine with an azide group at the end (polymer 1, with a molecular weight of 3 kDa) as a side backbone in a procedure for synthesis of a side chain. The first three steps belong to the procedure for synthesis of the side chain. Firstly, the reaction between the amino groups on the poly-L-lysine and the active ester is used to graft the active ester-polyethylene glycol-biotin to the poly-L-lysine at a grafting ratio of 50% to obtain polymer 2 (Formula 1). Afterwards, an excess of active ester-polyethylene glycol-methyl is added to the reaction to obtain polymer 3 (Formula 2) to ensure that there are no remaining amino groups on the poly-L-lysine. The next step is to connect the polyethylene glycol-active ester to the end of poly-L-lysine through the reaction between the azide group and the alkynyl group (click chemistry) to obtain polymer 4 (Formula 3). Because polymer 4 is introduced with active ester, it can be grafted to the main backbone poly-L-lysine (15-30 kDa) smoothly according to a grafting ratio of 40% to obtain polymer 5 (PETx) (Formula 4).

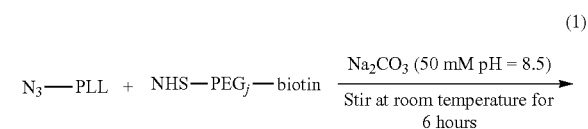
(1)

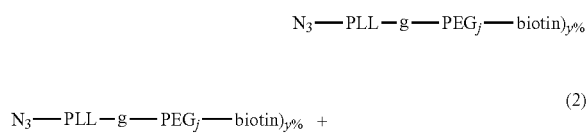
(2)

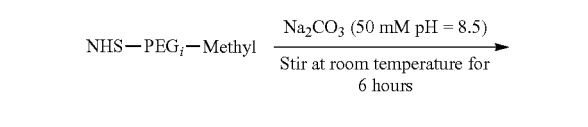
(3)

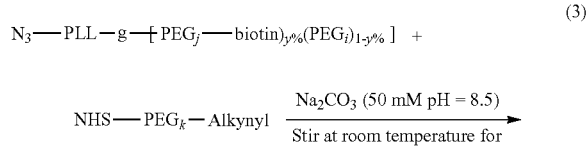
(4)

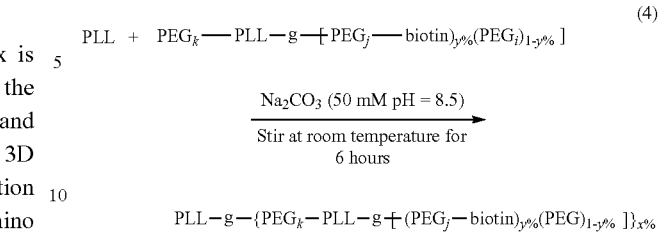

Figure 5:
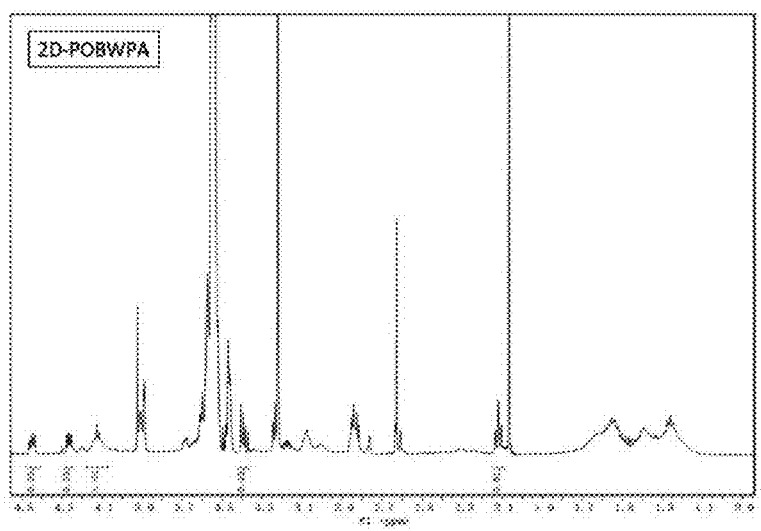
FIG. 5 is an NMR spectrum of polymer 3.

FIG. 5 is an NMR spectrum of polymer 3: ($^1$H NMR in D$_2$O δ [ppm]=1.34-1.43 (lysine γ-CH$_2$), (biotin, β-CH$_2$—), 1.47-1.87 (lysine β, δ-CH$_2$), (biotin, γ-CH$_2$), 2.15 (biotin, —CH$_2$C(O)NH—), 2.51 (coupled PEG, —CH$_2$—C(O)—N), 2.68 (lysine, (—CH$_2$—C(O)—N)), 2.82-2.89 (lysine, —CH$_2$—NH—C(O)), (PEG, —CH$_2$—NH—C(O)), 3.07 (biotin, —S—CH$_2$—), 3.21 (biotin, —S—CH—), 3.27 (free lysine, —N—CH$_2$), 3.38 (PEG, —O—CH3), 3.56 (PEG, CH$_2$—O—), 4.13 (lysine, N—CH—C(O)—), 4.27 and 4.45 (biotin, 2 bridge head CH)).

Figure 6:
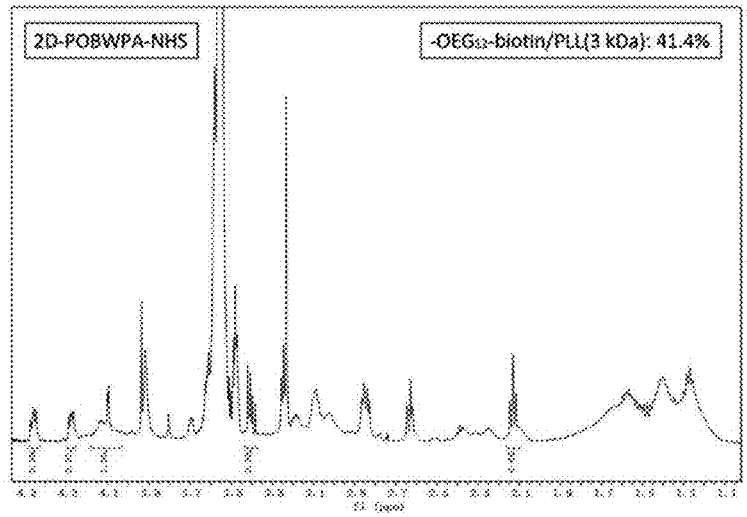
FIG. 6 is an NMR spectrum of polymer 4.

FIG. 6 is an NMR spectrum of polymer 4: ($^1$H NMR in D$_2$O, δ [ppm]=1.32-1.41 (lysine γ-CH$_2$), (biotin, β-CH$_2$—), 1.48-1.89 (lysine β, δ-CH$_2$), (biotin, γ-CH$_2$), 2.16 (biotin, —CH$_2$C(O)NH—), 2.52 (coupled PEG, —CH$_2$—C(O)—N), 2.69 (lysine, (—CH$_2$—C(O)—N)), 2.83-2.91 (lysine, —CH$_2$—NH—C(O)), (PEG, —CH$_2$—NH—C(O)), 3.09 (biotin, —S—CH$_2$—), 3.23 (biotin, —S—CH—), 3.26 (free lysine, —N—CH$_2$), 3.37 (PEG, —O—CH$_3$), 3.55 (PEG, CH$_2$—O—), 4.15 (lysine, N—CH—C(O)—), 4.26 and 4.47 (biotin, 2 bridge head CH)).

Figure 7:
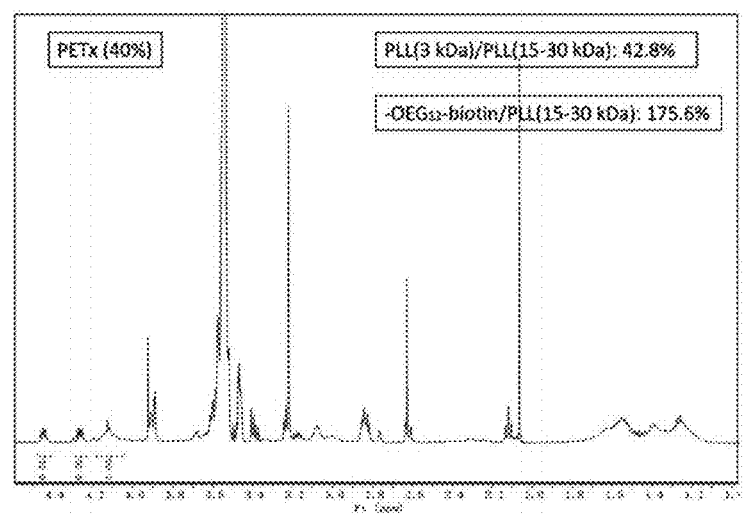
FIG. 7 is an NMR spectrum of a polymer PETx whose biological recognition group is exemplified by biotin.

FIG. 7 is an NMR spectrum of the polymer PETx: ($^1$H NMR in D$_2$O, δ [ppm]=1.34-1.42 (lysine γ-CH$_2$), (biotin, β-CH$_2$—), 1.44-1.89 (lysine β, δ-CH$_2$), (biotin, γ-CH$_2$), 2.13 (biotin, —CH$_2$C(O)NH—), 2.54 (coupled PEG, —CH$_2$—C(O)—N), 2.71 (lysine, (—CH$_2$—C(O)—N)), 2.84-2.92 (lysine, —CH$_2$—NH—C(O)), (PEG, —CH$_2$—NH—C(O)), 3.10 (biotin, —S—CH$_2$—), 3.23 (biotin, —S—CH—), 3.25 (free lysine, —N—CH$_2$), 3.36 (PEG, —O—CH3), 3.57 (PEG, CH$_2$—O—), 4.13 (lysine, N—CH—C(O)—), 4.26 and 4.46 (biotin, 2 bridge head CH)).

Figure 8:
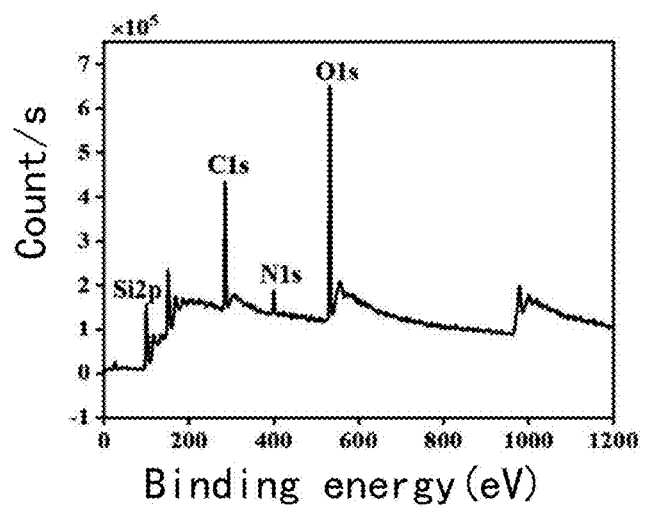
FIG. 8 is an XPS spectrum of a PETx film on a silica surface.

FIG. 8 is an XPS spectrum of a PETx film on a silica surface, showing the composition of various elements of PETx.

Figure 9:
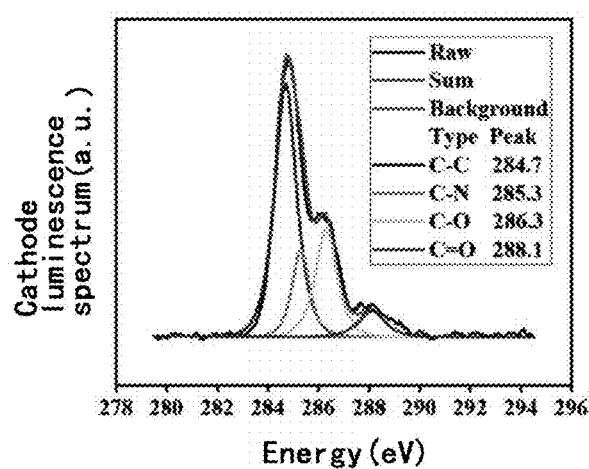
FIG. 9 is a high-resolution C1s XPS spectrum of a PETx film on a silica surface.

FIG. 9 is a high-resolution C1s XPS spectrum of a PETx film on a silica surface, indicating the valence type of each carbon element.

Example 2

Figure 10:
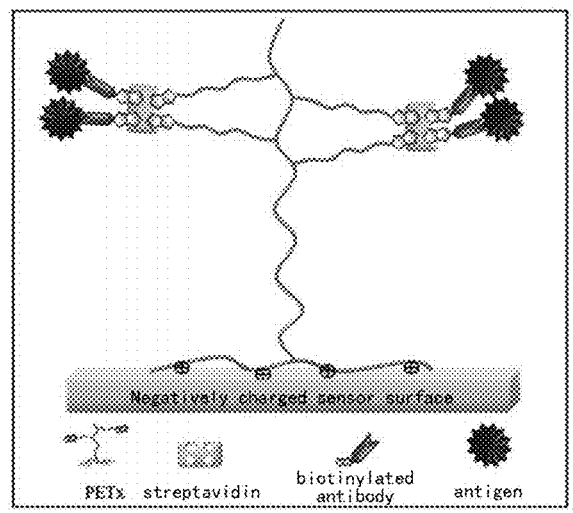
FIG. 10 shows the principle of biodetection of PETx whose biological recognition group is exemplified by biotin.

We compared the biodetection effects of PETx and 2D PLL-g-PEG-biotin by optical interferometry. The working principle of the product of the present invention is shown in FIG. 10. First, PETx is modified on the end face of the negatively charged optical fiber, and then the PETx can specifically adsorb streptavidin, and then streptavidin can specifically adsorb biotinylated anti-human IgG antibody (NNCrystal company), and finally the antibody can specifically detect an antigen.

Figure 11:
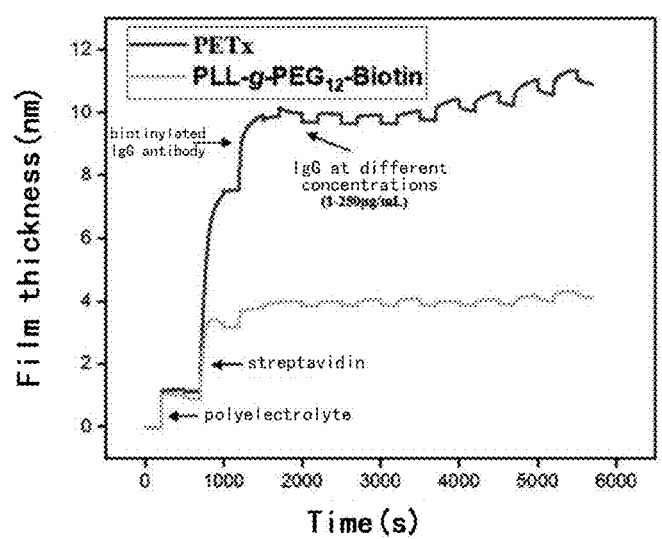
FIG. 11 is a comparison diagram of real-time biodetection between PETx whose biological recognition group is exemplified by biotin and 2D interface.

FIG. 11 shows real-time detection effects of PETx and PLL-g-PEG-Biotin protein. The ordinate is the thickness of the film formed on the end face of the fiber. From the figure, we found that when detecting an excess of streptavidin (200 nM), PETx can bind more streptavidin. This is due to the fact that PETx contains more biological recognition groups (biotin). After that, the sensor detected antigens (human immunoglobulin, human IgG, NNCrystal) at different concentrations (1-250 μg/mL).

Figure 12:
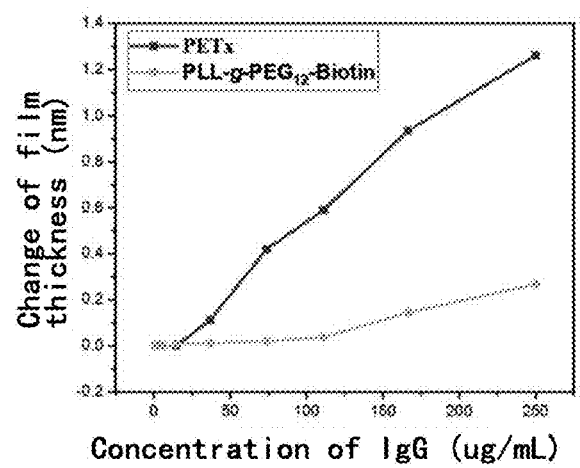
FIG. 12 is a comparison diagram of the concentration curves of real-time biodetection of PETx whose biological recognition group is exemplified by biotin and 2D interface.

FIG. 12 is a graph of the concentration curves for detection of antigen by two types of sensing interfaces, and the slopes of the curves reflect the sensitivity of the sensor. It can be found in the figure that the sensitivity of the sensor modified by PETx is much higher than that of the traditional 2D interface sensor (PLL-g-PEG-biotin).

Example 3

We compared the anti-nonspecific adsorption ability of PETx and other polyelectrolytes (PLL-g-PEG-biotin and PLL) by optical interferometry. We first modified PETx on the end face of the negatively charged optical fiber, and then tested the anti-nonspecific adsorption abilities of the end face of the optical fiber in the bovine serum albumin (BSA) solution and serums of different dilutions.

Figure 13:
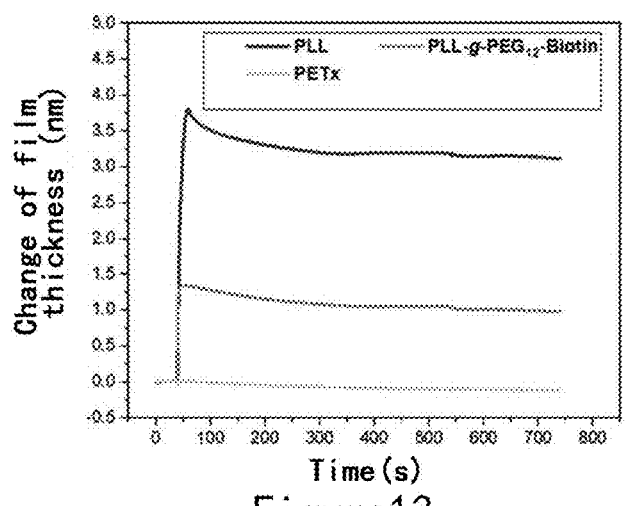
FIG. 13 shows an anti-nonspecific adsorption experiment of PETx whose biological recognition group is exemplified by biotin and other polyelectrolytes in bovine serum albumin solution.

FIG. 13 shows an anti-nonspecific adsorption experiment of PETx whose biological recognition group is exemplified by biotin and other polyelectrolytes in BSA solution (15 μM, 10 mM HEPES, pH 7.4). The ordinate is the thickness change of the film formed on the end face of the optical fiber. It can be seen from the figure that the thickness of the end face of the optical fiber modified with PETx did not increase after being immersed in the BSA solution. This shows that PETx has a perfect anti-nonspecific adsorption ability.

Figure 14:
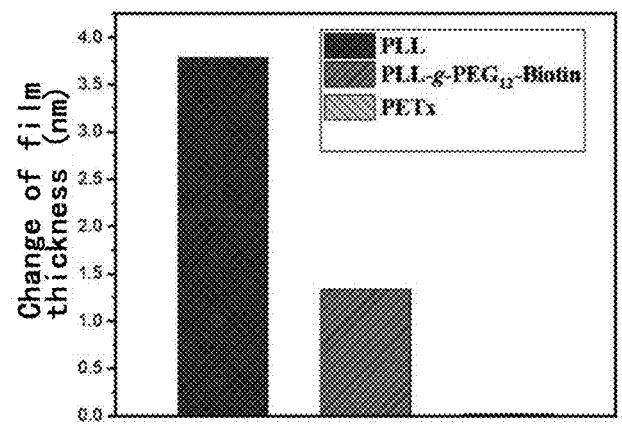
FIG. 14 is a comparison diagram of the anti-nonspecific adsorption effects of PETx whose biological recognition group is exemplified by biotin and other polyelectrolytes in bovine serum albumin solution.

FIG. 14 intuitively compares anti-nonspecific adsorption effects of PETx and other polyelectrolytes in BSA solution.

Figure 15:
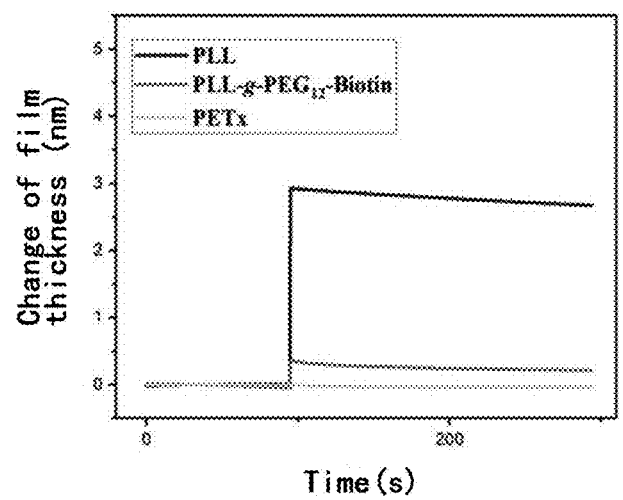
FIG. 15 shows an anti-nonspecific adsorption experiment of PETx whose biological recognition group is exemplified by biotin and other polyelectrolytes in 10% serum.

FIG. 15 shows an anti-nonspecific adsorption experiment of PETx whose biological recognition group is exemplified by biotin and other polyelectrolytes in 10% serum. We first immersed the PETx-modified end face of the optical fiber in HEPES buffer to measure the baseline. After that, the end face of the optical fiber was immersed in 10% serum and taken out after 5 minutes. The end face of the optical fiber taken out was immersed in HEPES buffer again, and the change of the baseline was observed. As shown in the figure, the baseline of the PETx-modified end face of the optical fiber did not rise. This shows that PETx has a perfect anti-nonspecific adsorption ability.

Figure 16:
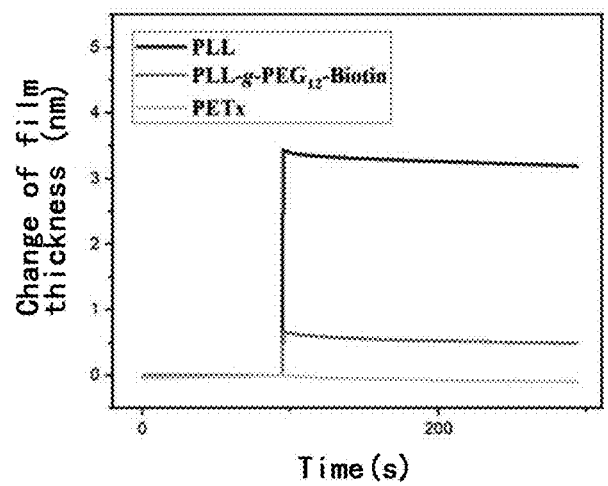
FIG. 16 shows an anti-nonspecific adsorption experiment of PETx whose biological recognition group is exemplified by biotin and other polyelectrolytes in 50% serum.

FIG. 16 shows an anti-nonspecific adsorption experiment of PETx whose biological recognition group is exemplified by biotin and other polyelectrolytes in 50% serum. We first immersed the PETx-modified end face of the optical fiber into HEPES buffer to measure the baseline. After that, the end face of the optical fiber was immersed in 50% serum and taken out after 5 minutes. The end face of the optical fiber taken out was immersed in HEPES buffer again, and the change of the baseline was observed. As shown in the figure, the baseline of the PETx-modified end face of the optical fiber did not rise. This shows that PETx has a perfect anti-nonspecific adsorption ability.

Figure 17:
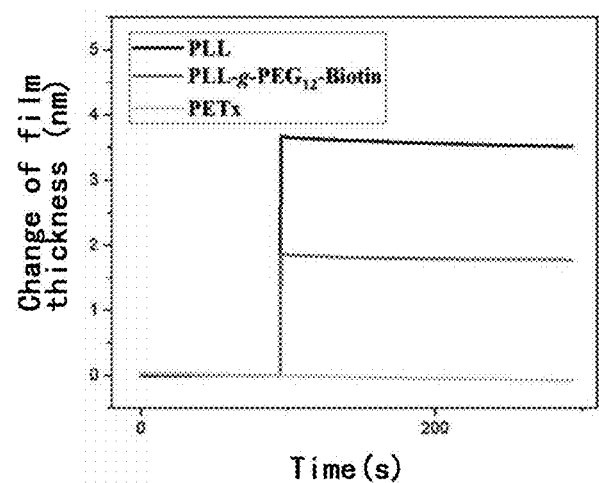
FIG. 17 is an anti-nonspecific adsorption experiment of PETx whose biological recognition group is exemplified by biotin and other polyelectrolytes in 100% serum.

FIG. 17 shows an anti-nonspecific adsorption experiment of PETx whose biological recognition group is exemplified by biotin and other polyelectrolytes in 100% serum. We first immersed the PETx-modified end face of the optical fiber into HEPES buffer to measure the baseline. After that, the end face of the optical fiber was immersed in 100% serum and taken out after 5 minutes. The end face of the optical fiber taken out was immersed in HEPES buffer again, and the change of the baseline was observed. As shown in the figure, the baseline of the PETx-modified end face of the optical fiber did not rise. This shows that PETx has a perfect anti-nonspecific adsorption ability.

Figure 18:
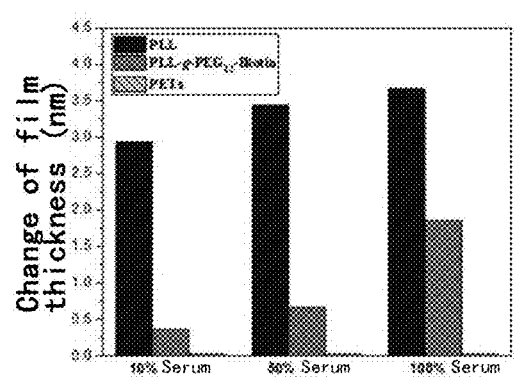
FIG. 18 is a comparison diagram of anti-nonspecific adsorption effects of PETx whose biological recognition group is exemplified by biotin and other polyelectrolytes in serums under different dilution conditions.

FIG. 18 intuitively compares anti-nonspecific adsorption effects of PETx and other polyelectrolytes in serums of different dilutions. The figure shows that PETx has an excellent anti-nonspecific adsorption ability in serums of different dilutions.

This scheme designs and synthesizes a new type of polyelectrolyte PETx, which can form a 3D sensing interface, and has more biotin functional groups and greater content of polyethylene glycol than the traditional 2D PLL-g-PEG-biotin. This makes PETx have a better sensing effect and a better ability to resist nonspecific adsorption.

The above descriptions are only the preferred embodiments of the present invention, and are not used to limit the present invention. Any modification, equivalent replacement, improvement, etc. made within the spirit and principle of the present invention shall be included within the scope of the present disclosure.

The invention claimed is:

1. A PETx polymer comprising a main backbone which is a first poly-L-lysine, and a side chain which is sequentially connected with a first polyethylene glycol and a second poly-L-lysine, the second poly-L-lysine is saturately connected with a second polyethylene glycol and a third polyethylene glycol without remaining amino groups, and the third polyethylene glycol is connected with a functional group at its end, wherein the first poly-L-lysine and the second poly-L-lysine have the same or different chain lengths, the first polyethylene glycol, the second polyethylene glycol and the third polyethylene glycol have the same or different chain lengths, and wherein the PETx polymer is PLL-g-$\{PEG_k$-PLL-g-$[(PEG_j$-functional group$)_y$ % $(PEG_i)_{1-y}$ %$]\}_x$ %, and the PETx polymer has the general formula:

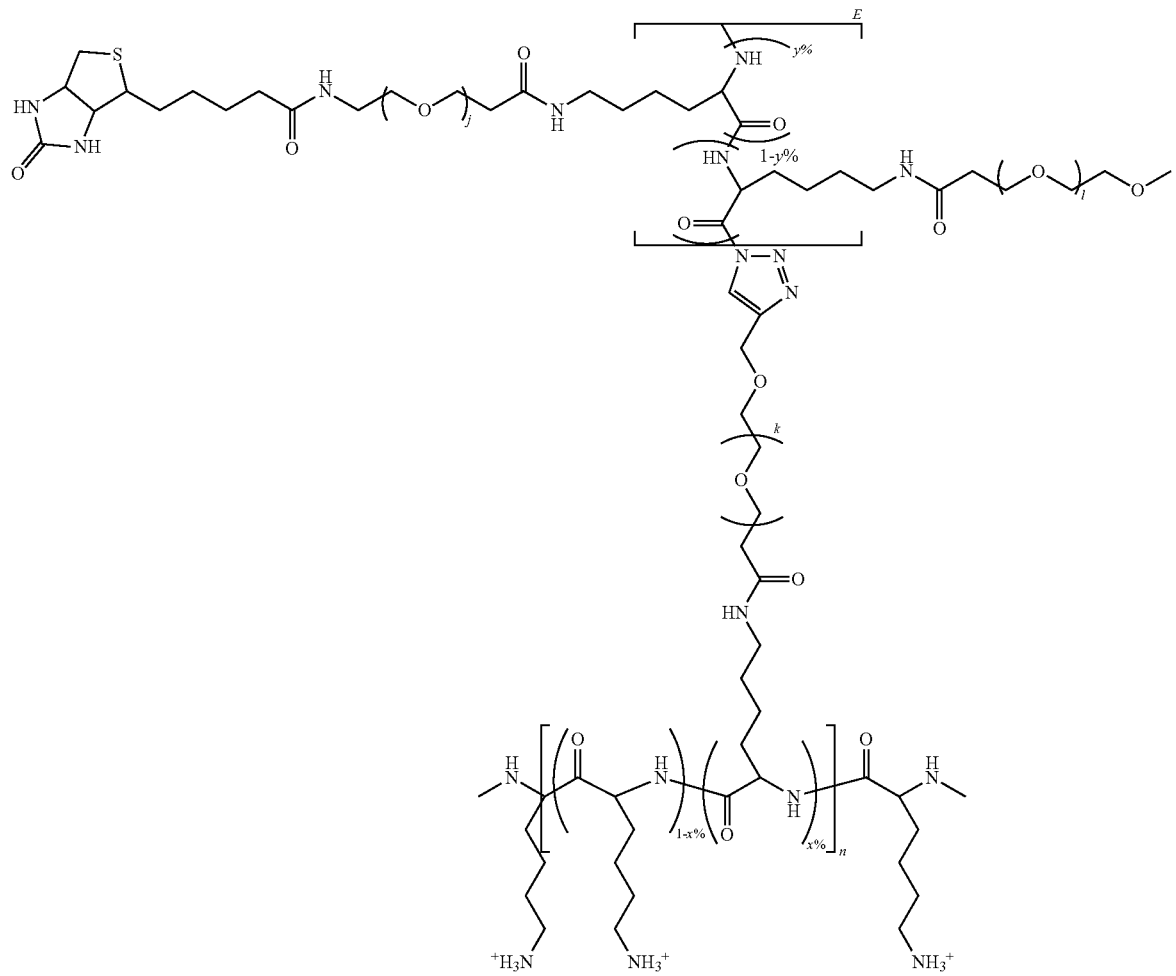

where i, j, k, m and n are all integers greater than or equal to 1, and x and y are in the range greater than 0 and less than 100.

2. The PETx polymer according to claim 1, wherein the functional group is selected from biotin, Ni-NTA or single-stranded DNA.

3. The PETx polymer according to claim 1, wherein the functional group is biotin.

4. The PETx polymer according to claim 1, wherein the first poly-L-lysine has a grafting ratio which does not exceed 40%.

5. The PETx polymer according to claim 1, wherein the first poly-L-lysine has a molecular weight of 15-30 kDa; and the second poly-L-lysine has a molecular weight of 3 kDa.

6. A method for preparing a PETx polymer, comprising: 1) by using a reaction between amino groups of polymer 1 ($N_3$-PLL or alkynyl-PLL) and active ester, grafting an active ester-polyethylene glycol-functional group (NHS-PEG-functional group) onto a polymer 1 ($N_3$-PLL or alkynyl-PLL) to obtain a polymer 2 ($N_3$-PLL-g-(PEG$_j$-functional group)$_{y\ \%}$ or alkynyl-PLL-g-(PEG$_j$-functional group)$_{y\ \%}$) (reaction 1); 2) adding excessive active ester-polyethylene glycol-methyl (NHS-PEG-methyl) to the reaction to obtain a polymer 3 ($N_3$-PLL-g-[(PEG$_j$-functional group)$_{y\ \%}$(PEG$_i$)$_{1-y\ \%}$] or alkynyl-PLL-g-[(PEG$_j$-functional group)$_{y\ \%}$)(PEG$_i$)$_{1-y\ \%}$] (reaction 2); 3) by using a click reaction between azide groups and alkynyl groups, grafting the polyethylene glycol-active ester (PEG-NHS) to the end of the poly-L-lysine in the polymer 3 to obtain a polymer 4 (NHS-PEG$_k$-PLL-g-[(PEG$_j$-functional group)$_{y\ \%}$ (PEG$_i$)$_{1-y\ \%}$]) (reaction 3); 4) grafting the polymer 4 to the main backbone poly-L-lysine with a grafting ratio not exceeding 40% to obtain polymer 5 (PETx, i.e. PLL-g-{PEG$_k$-PLL-g-[(PEG$_j$-functional group)$_{y\ \%}$(PEG$_i$)$_{1-y\ \%}$]}$_{x\ \%}$) (reaction 4),

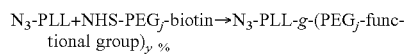

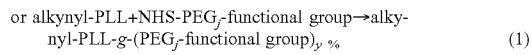     (1)

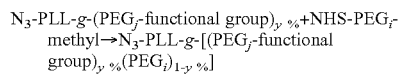

or

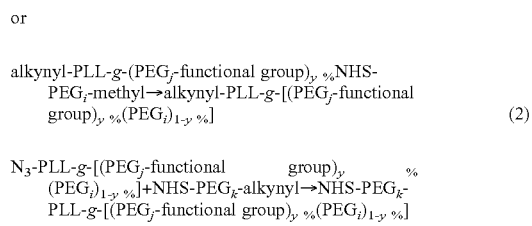     (2)

or alkynyl-PLL-*g*-[(PEG$_j$-functional group)$_y$ $_\%$ (PEG$_i$)$_{1-y}$ $_\%$]NHS-PEG$_k$-N$_3$→NHS-PEG$_k$-PLL-*g*-[(PEG$_j$-functional group)$_y$ $_\%$(PEG$_i$)$_{1-y}$ $_\%$]  (3)

PLL+NHS-PEG$_k$-PLL-*g*-[(PEG$_j$-functional group)$_y$ $_\%$(PEG$_i$)$_{1-y}$ $_\%$]→PLL-*g*-{PEG$_k$-PLL-*g*-[(PEG$_j$-functional group)$_y$ $_\%$(PEG$_i$)$_{1-y}$ $_\%$]}$_x$ $_\%$  (4)

where i, j, k, m, and n are all integers greater than or equal to 1, and x and y are both in the range greater than 0 and less than 100.

7. A three-dimensional thorn-like sensor interface comprising a negatively charged sensor surface and the PETx polymer according to claim 1, wherein the PETx polymer is modified to the sensor surface by electrostatic action, thereby forming the three-dimensional thorn-like sensing interface.

8. The three-dimensional thorn-like sensor interface according to claim 7, wherein the sensor surface is an optical fiber sensor surface, a silica sensor surface, a metal sensor surface, or a metal oxide sensor surface.

9. The three-dimensional thorn-like sensor interface according to claim 7 further comprising using the three-dimensional thorn-like sensor interface.

\* \* \* \* \*